(12) United States Patent
Grey et al.

(10) Patent No.: US 6,929,154 B2
(45) Date of Patent: Aug. 16, 2005

(54) SECURE DISPENSING APPARATUS

(75) Inventors: Matthew James Grey, New Haw (GB); Martin Philip Riddiford, London (GB); Geoffrey Guy, Salisbury (GB)

(73) Assignee: GW Pharma Limited, Salisbury (GB)

( * ) Notice: Subject to any disclaimer, the term of this patent is extended or adjusted under 35 U.S.C. 154(b) by 37 days.

(21) Appl. No.: 10/399,573

(22) PCT Filed: Oct. 22, 2001

(86) PCT No.: PCT/GB01/04681
§ 371 (c)(1),
(2), (4) Date: Nov. 10, 2003

(87) PCT Pub. No.: WO02/32784
PCT Pub. Date: Apr. 25, 2002

(65) Prior Publication Data
US 2004/0065685 A1 Apr. 8, 2004

(30) Foreign Application Priority Data
Oct. 20, 2000 (GB) .......................... 00258111

(51) Int. Cl.⁷ ............................... B67D 5/32
(52) U.S. Cl. .................... 222/153.03; 222/153.05; 222/153.11; 222/402.1
(58) Field of Search .............. 222/153.03, 153.05, 222/153.11, 153.13, 402.1

(56) References Cited

U.S. PATENT DOCUMENTS 3,738,537 A * 6/1973 Gach ................. 222/153.11
5,310,086 A * 5/1994 Julinot ................... 222/1
5,842,601 A * 12/1998 Pierpoint .................. 222/1
5,842,602 A * 12/1998 Pierpoint .................. 222/1

FOREIGN PATENT DOCUMENTS

GB         1005768 A        9/1965

* cited by examiner

Primary Examiner—Joseph A. Kaufman
(74) Attorney, Agent, or Firm—Wolf, Greenfield & Sacks, P.C.

(57) ABSTRACT

Secure dispensing apparatus is described which is adapted to dispense e.g. a prescription drug from an axial compression dispensing device (1). This is located in a housing (10) including a dispensing aperture (16). The axial compression dispensing device (1) is located in a central chamber of axial length slightly longer than that of the axial compression dispensing device, and structures (30) are provided at one end of the chamber movable with respect thereto to compress the axial compression dispensing device to cause dispensing via the dispensing aperture (16). The structures (30) comprises a central breakable axial stem (33) attached to a pressure plate (34), the pressure plate having a surface configuration on its side facing away from the axial compression dispensing device providing a set of surfaces (35) not in a plane transverse to the axis of the breakable stem, and apertures (36) in the end of the outer housing aligned with the set of surfaces of the pressure plate and none of the apertures (36) being coaxial with the breakable stem (33). Structures such as a wall (15) are provided to limit the amount of movement of the pressure plate (34) away from the end (11) of the outer housing containing the set of apertures (36).

22 Claims, 6 Drawing Sheets

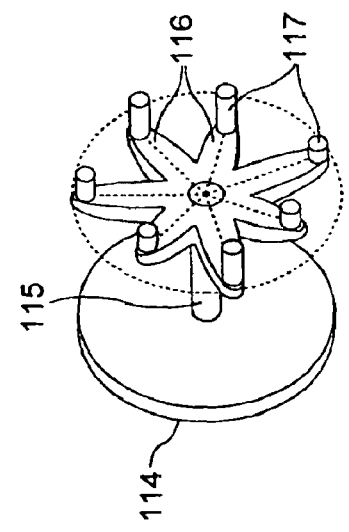
FIG. 10
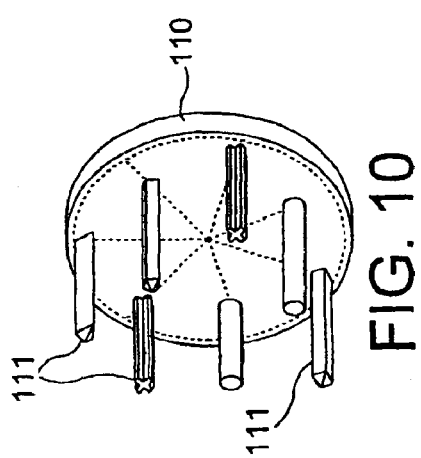
FIG. 11
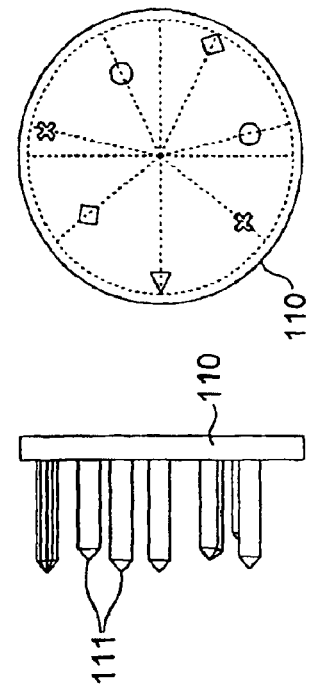
FIG. 12
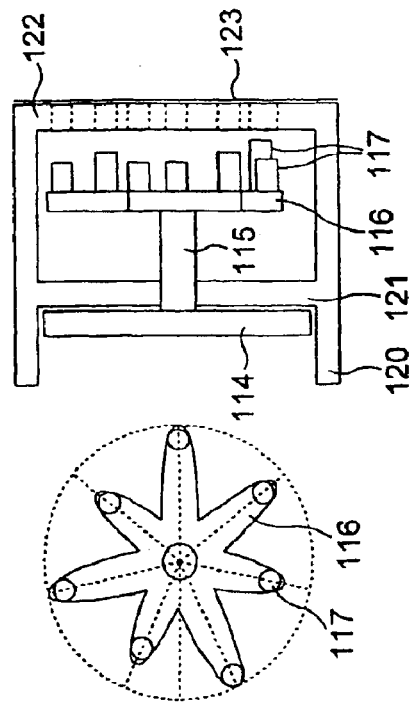

SECURE DISPENSING APPARATUS

This invention relates to the secure dispensing of materials and particularly to the packaging of dangerous products such as drugs, poisons, toxic materials or the like.

There are numerous circumstances in which it is desired to, able to dispense materials in a secure fashion, in particular in order to restrict the amount of material dispensed on the one hand and separately to prevent access to the entire quantity of material save by someone entitled or authorised to dispense such material, for example for self-medication.

It has long been recognised that packaging can play an important part in securing, for example, drugs against being consumed by children. There are numerous packaging designs which are designed with "child-proof" closures.

While these may provide a certain degree of effectiveness, once the closure is opened, there is generally then no further barrier to access to the entire content of the container and thus to whatever material is within. This is clearly unsatisfactory and potentially unsafe.

The present invention provides an alternative approach, which is particularly suited to the dispensing of doses of materials presented in a dosable form in some sort of elongate or discoid container or cassette from which a quantity or unit of material can then be dispensed by axial or rotary movement and wherein the axial movement can be translated into e.g. a rotational movement by a standard mechanism. By way of example only, taken from the field of pharmaceuticals, though the area of application of the invention is rather wider, elongate sealed canisters are widely used for the dispensing of drugs for asthmatics, with the inside of the canister being under pressure and containing a liquid material which may be dispensed as an aerosol spray by placing an axial outlet tube forming part of the canister into an aerosol nozzle and depressing the nozzle with respect to the main body of the canister. GB-A-206116 and WO 96/27655 disclose typical such systems. Pump action dispensers for pasty materials such as toothpaste are known which likewise are actuated by axial pressure on an elongate container, and recently homeopathic medicines have been dispensed in elongate cylindrical containers which contain an internal mechanism enabling the dispensing one-by-one of small pills of homeopathic remedy contained within the housing. Perfumes may be dispensed using a pressurised "refill" container in analogous fashion (see, e.g. GB-A-1005768), and similar dispensing systems are known for disarming sprays (e.g. U.S. Pat. No. 5,310,086). In all of these cases, dispensing is achieved by axial compression of the container containing the material it is desired to dispense. Such a form of container is denoted herein by the term "axial compression dispensing device".

In accordance with the present invention, there is provided a secure dispensing apparatus which comprises a dispensing device surrounded by a housing, the housing having an aperture registered with a dispensing aperture of the dispensing device, and the dispensing device being actuatable to dispense a dose of material contained within it by a rectilinear movement of an actuation member relative to the housing and acting upon a part of the dispensing device, and wherein between the actuation member and the part of the dispensing device there is located a force-transmitting member having at least one elongate breakable stem located substantially parallel to the direction of movement of the actuation member, and the stem(s) being connected to a pressure plate having a surface configuration on its side facing away from the stem(s) providing a set of surfaces not in a plane transverse to the axis of the stem(s), and wherein the housing has a set of apertures aligned with the set of surfaces on the pressure plate and means for limiting the amount of movement of the force-transmitting member. Preferably the force transmitting member has a single stem.

The dispensing apparatus is of particular value when the dispensing device is an axial compression dispensing device, where the housing may include a central chamber surrounding the axial compression dispensing device and of axial length slightly longer than that of compression dispensing device, and the force transmitting member is located at one end of the chamber movable with respect thereto to compress an axial compression dispensing device located within the chamber, whereby to cause dispensing via the dispensing aperture. In such a case, the apertures in the housing are at one end and aligned with the set of surfaces of the pressure plate, with none of the apertures being coaxial with the breakable stem(s). Means may be provided to limit the amount of movement of the pressure plate away from the end of the housing containing the set of apertures.

Such a presentation for containing a dispensable material is highly secure. In order to dispense the material, the set of surfaces on the pressure plate must be subjected to from outside the housing by application thereto of elongate members inserted through the apertures in the wall or end of the housing in such a way that the force applied to the pressure plate at the set of surfaces, all of which are spaced away from the axis of the stem are such as to cause the pressure plate to move in a direction parallel to the axis of the breakable stem(s). Because the set of surfaces of the pressure plate accessible through the apertures do not lie in a plane transverse to the axis of the stem(s), this means that in order to cause the plate to move in the direction of the axis of the stem, pressure must be applied to it evenly by two or more elongate members inserted through the apertures, but inserted by different degrees. If it is attempted to move the plate axially by pushing on it unevenly, for example by inserting just a single elongate member through one of the apertures in the housing, the pressure plate will swivel causing the stem(s) to snap. Once the stem(s) are snapped, it can no longer transmit force via the stem, e.g. to one end of an axial compression dispensing device, and accordingly, because the pressure plate cannot move far enough away from the end of the housing in which the set of apertures are located, that device cannot be compressed and nothing can be dispensed. The contents of the device are accordingly protected against access by unauthorised persons or children, for example.

It will be seen at once that if a "key" consisting of a base member bearing a number of elongate members parallel with one another and of different lengths, the end points of the members being located in a configuration matching the configuration of the set of surfaces of the pressure plate, is inserted through the apertures in the housing, and moved in the direction of the axis of the stem(s), pressure will be applied evenly to the pressure plate and dispensing will take place. The lengths of the individual elongate members forming part of such a key can be thought of as analogous to the depths of V-shaped grooves cut into keys for operating a standard "cylinder lock". In that case, the lock can only be opened when spring transversely split axially movable pins are individually located so that the splits in them line up flush with the wall of a block in which the cylinder may be turned with the key. They line up flush when the correct key is inserted. With an incorrect key inserted, one or more of the transversely split pins has its transverse split otherwise than at the surface of the cylinder and the pin accordingly acts to prevent the cylinder being turned and thus the lock being opened. In the device in accordance with the invention, an analogous process is used to ensure that the correct "key" will enable the requisite force for dispensing to be transmitted, in the case of an axial compression dispensing device for that to be axially compressed. Use of an incorrect key, or trying to cause such dispensing without having a key, will result in the fracture of the stem(s) of the member adapted to enable dispensing to take place and accordingly render the device safe. The key may be an integral unit of base member and elongate members or, for example, may be apparatus having a set of differentially advanceable elongate members which act, when appropriately advanced, in analogous fashion.

A wide variety of keys may be produced to match a wide variety of pressure plates and outer casing aperture patterns. Preferably the number of apertures is 5 to 7 and preferably these are substantially equiangularly spaced around the axis of the frangible stem, most preferably substantially equidistantly from the axis of that stem in a radial direction. The shape of the apertures may vary, and a single key may have means to pass through the apertures of likewise varied shape, e.g. round, square, triangular or cruciform in cross-section.

It will be clear that in the case of an axial compression dispensing device the act of dispensing depends heavily on being able to exert direct axial pressure on it and that in turn depends on exerting accurately axial pressure on the pressure plate. If the housing is to be held in the hand and the key simply pushed in at the end remote from the dispensing aperture, this can be achieved by dimensioning the apertures in the end wall of the outer casing which covers the pressure plate so that they act as guide elements, preferably with the wall thickness of the end of the housing greater than the transverse measurement of the elongate members on the "key" which are to come into contact with the set of locations on the side of the pressure plate remote from the axial compression dispensing device. It is also important to ensure that the axial compression dispensing device is a relatively close fit in the housing. If the device is externally a simple cylinder, then a plain cylindrical cavity in the housing is sufficient. If, for example, because it has an enlarged cap portion, the exterior of the device is a stepped cylinder, the housing interior may be correspondingly stepped, e.g. with a wider portion to accommodate the end cap and a narrower part to give good guidance to the body of the device.

Alternatively, if the apparatus is to be used in a dispenser which is e.g. adapted to maintain a record of dosage times, or to prevent dosage save at predetermined intervals, such as described in our patent application filed simultaneously with this application, then the key may be fitted in the dispenser and the apparatus likewise fitted in the dispenser, e.g. in a tubular close-fitting channel therein, conveniently with a pin and slot location to ensure correct alignment around the long axis of the apparatus. In this case, the dispenser provides accurate guidance even if the holes are larger than the pins on the key. If, prior to first use, the holes are covered with a frangible seal, the pins pierce the seal on first use. Such a seal is valuable as showing evidence of tampering if, for example, someone has tried to cause the apparatus to dispense a medicament without using the dispenser which contains the correct key.

The dispensing devices of the present invention are particularly useful as replaceable drug-containing units in dispensing apparatus which may be configured to move the "key" in known fashion to dispense an appropriate dose of material. If the drug dispensed by a pharmacist is presented in such a secure fashion, together with a key, the key and dispensing container can be separated from one another and someone who comes across the dispensing container will not be able to dispense any material from it unless they also have the key.

The invention is illustrated by way of example with reference to the accompanying drawings in which.

Figure 13C:
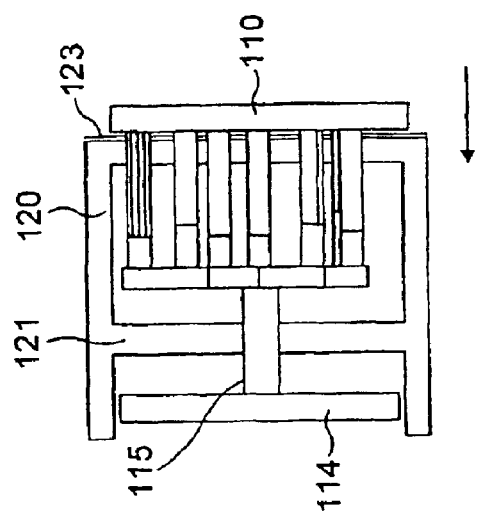
Figure 13B:
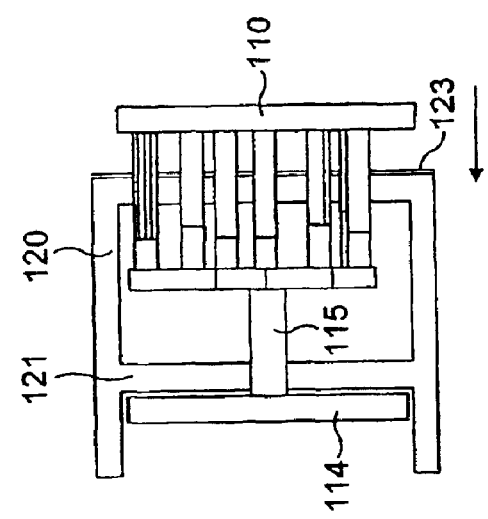
Figure 13A:
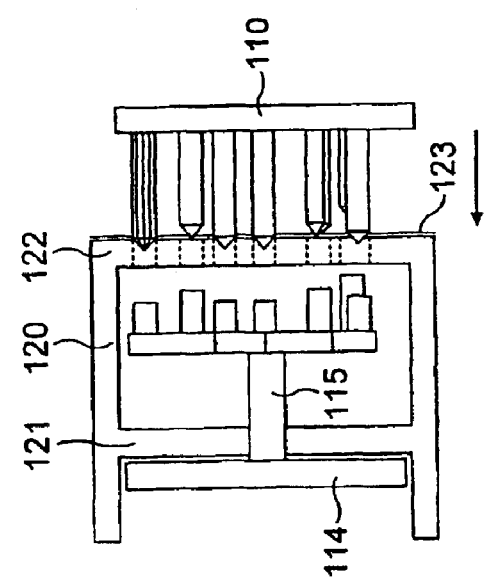

FIGS. 6 to 9 inclusive show similar views to FIGS. 2 to 8, but in connection with an alternate design of drug-dispensing actuation device;

FIGS. 10 and 11 show in perspective view a key and corresponding pressure plate assembly;

FIG. 12 shows the key and pressure plate assembly in side view and aligned with diagrammatic end views of each, and FIGS. 13a to c show three stages of use of the key, diagrammatically.

Figure 1:
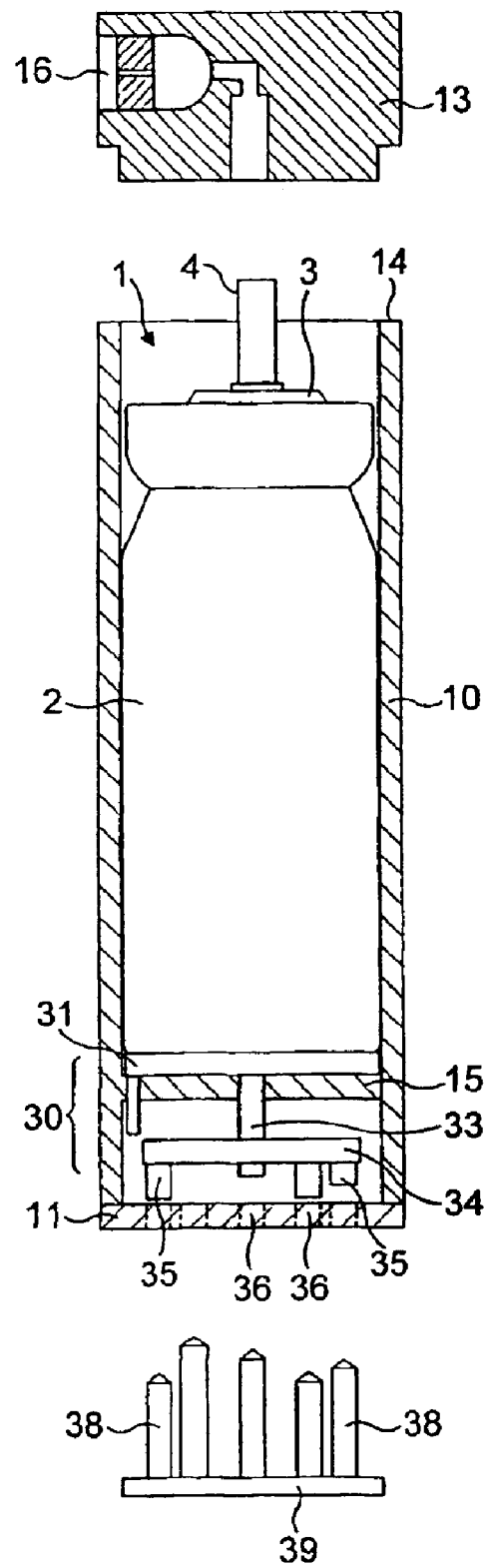
FIG. 1 is a diagrammatic sectional view of a secure dispensing device in accordance with the present invention.

Referring first to FIG. 1, this shows in diagrammatic sectional form a simplified secure dosage container in accordance with the present invention. Denoted 1 is a standard small elongate pressurised aerosol container which has a generally cylindrical body 2 between a lower flat end and an upper end which is sealed by a swaged-on cover 3 carrying a valve housing with protruding valve stem 4. The contents are pressurised and there is a dip tube so that if valve stem 4 is moved downwards, material is dispensed from within pressurised container 1.

The outer housing consists of a generally cylindrical sleeve 10 having a transverse lower end wall 11, an intermediate apertured transverse wall 15 and a cap 13 which can be welded to the end of the cylindrical sleeve 10, e.g. at 14. Cap 13 includes an aerosol dispensing nozzle 16 of known design which is set substantially in the centre of the cap and aligned appropriately with a transverse passage in the cap through which the nozzle can be seen in the drawing. Cap 13 is e.g. ultrasonically welded to the edge 14 of cylindrical portion 10 when the outer housing is assembled around the canister 2 and a plate and stem member generally denoted 30 shown in the drawing.

Plate and stem member 30 consists of, as seen in the drawing, an upper plate 31 adapted to contact the underside of body 2, a fracturable axial stem 33, and a lower plate 34 from which project a number (four are as shown in the drawing) of downwardly directed posts 35. These posts are of different downward axial extent and they are sized and located to match apertures 36 located in the end wall 11 of the outer casing. The stem member 30 passes through an aperture in the centre of transverse wall 15.

The dimensions of the various components are so chosen that when the cap 13 is ultrasonically welded to edge 14, the plate and stem member 30 and pressurised canister 2 effectively occupy substantially the entire axial length of the interior of the outer housing.

The thickness of end wall 11 is chosen such that apertures 36 may provide axial guidance to a set of prongs 38 located on a key disc 39. Prongs 38 are of different heights corresponding to the heights of downwardly depending posts 35 on disc 34, and the arrangement of the prongs 38 is such that they can be registered with holes 36 and the ends of prongs 38 then brought simultaneously into contact with the ends of posts 35. Further axial movement than that necessary to effect such contacting means that the disc 34 moves further away from wall 11, and disc 31 exerts pressure on the base of the pressurised canister 2 which, because it can move relative to the cap 13 which holds the nozzle, moves the dispensing tube 4 into the container, thus releasing material under pressure via nozzle 16.

If an attempt is made to effect such dispensing by pushing a prong through a single one of apertures 36, although it may contact the end of one of the downwardly depending posts 35, as soon as any pressure is applied, this will cause disc 34 to tilt, stem 33 to bend and then immediately break, and thereafter the pressure plate 31 cannot be raised by axial force transmitted through stem 33. Furthermore, it is not then possible to move canister 2 up by pushing a prong further in through hole 36, as plate 34 can only move up until it contacts the transverse fixed wall 15. Because the transverse wall 15 is fixed, although pushing a prong in through aperture 36 enables plate 34 to be abutted against wall 15, but not allow it to be moved any further, and in particular, because stem 33 is already broken, it does not allow pressure plate 31 to exert any pressure on the bottom of canister 2 which might effect dispensing.

As can be seen by contemplating FIG. 1, the secure dispensing container needs to be provided with a key to enable material to be dispensed from it, the key consisting of key disc 39 with the actuating posts 38 of different heights on it. An additional benefit of the particular presentation shown in FIG. 1 is that it is easy to position a seal across the end of wall 11 covering the apertures 36, which seal must be pierced by the prongs 38 when the dispensing device is first used, or which must be torn off in order to provide access to apertures 36 for posts 38. In either event, it is clear whether the dispensing device has been put to use or not.

Figure 2:
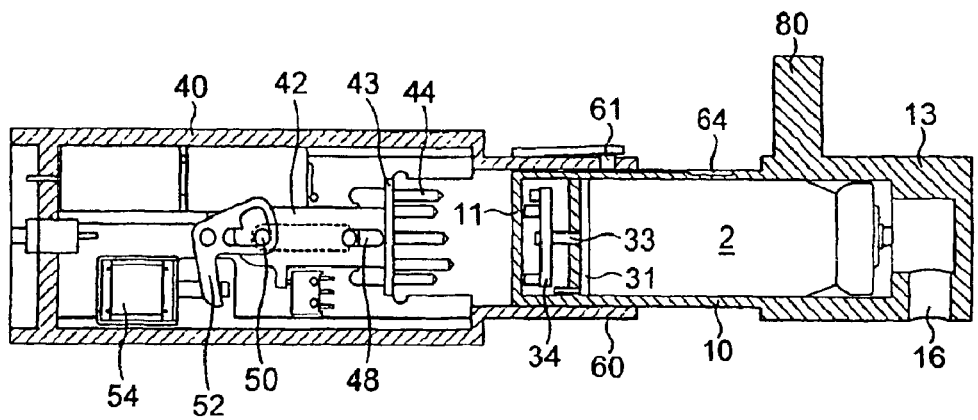
FIGS. 2, 3, 4 and 5 show a device in accordance with the present invention located in a dispenser actuation mechanism described in more detail below, FIGS. 2 to 5 showing the item in different positions of the dispensing device.

The device of FIG. 1 is shown in FIGS. 2 to 9 forming part of a drug-dispensing system into which the device may be inserted. Referring first to FIGS. 2 to 5, the system comprises a housing 40 containing within it an axially movable member 42 carrying at one end a key disc 43 having a number of different length prongs 44 protruding from it. Member 42 is guided axially within the housing and can be moved to the left of the position shown in FIG. 2 by a short distance determined by the length of a slot 48 therein. One end of member 42 bears a protruding pin 50 which is surrounded by an aperture formed in one end of a flat rocker arm 52, the position of which is controlled via a solenoid 54. In the position shown in FIG. 2, the member 42 can move axially to its fullest extent, while in the position shown in FIG. 5 with the solenoid actuated, the pin 50 can only move a short distance before coming to rest on a shoulder within the rocker plate 52. It should be understood that the side view shown shows only one pin 50 and rocker plate 52. The device has two such pins and plates, so the opposite side view of FIG. 2 is the same, though reversed in sense.

Figure 3:
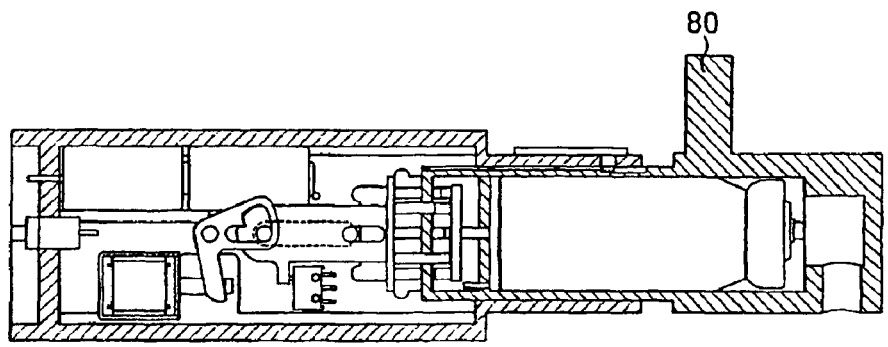

The entire dispensing unit is arranged to be slotted into a sleeve-like extension of housing 40, denoted 60 in FIG. 2, and it may be held captive therein by means of a spring bead 61 engaging in a preformed groove 64 running along the side of wall 10. The normally inserted position is shown in FIG. 3, with the bead 61 spring latched into the end of the groove 64 remote from cap 13 and nozzle 16. As can be seen at this point, the prongs 44 are passing through the end wall 11 of the dispensing unit and have come to rest against the left-hand ends as shown in the drawing of the prongs extending from plate 34. Accurate matching may be assisted by having each of the ends of the prongs on plate 34 with a depression in its end and making each of the prongs 44 somewhat pointed, as shown in the drawing.

Figure 4:
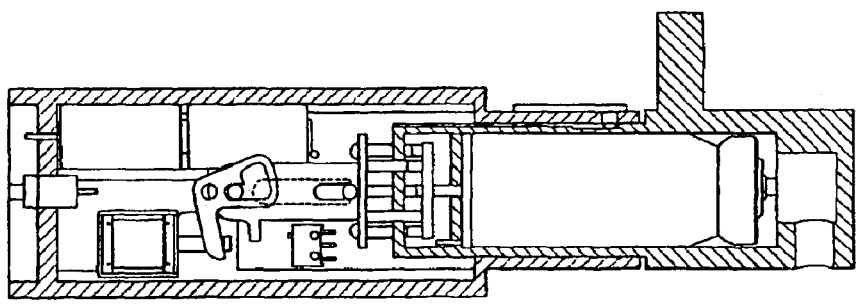

If the canister 2 is now moved towards the left as shown in FIG. 4 with the solenoid 54 unactuated, it simply moves axially slidable member 42 with it. Thus, there is no relative movement between outer housing 10 and the key disc 43 and its prongs 44. The reason for this is that, as noted above, pin 50 can move close to the axis about which rocker plate 52 can pivot.

Figure 5:
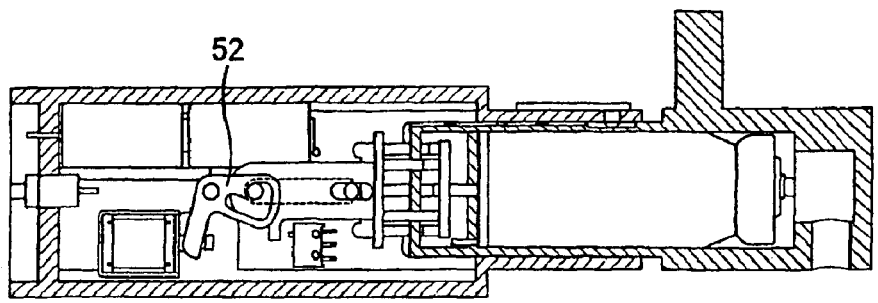

If dispensing via nozzle 16 is required, however, then the solenoid is actuated electrically by suitable means and the rocker plate 52 moves to the position shown in FIG. 5. In this position, as soon as the outer housing 10 is moved to the left as shown in that Figure, the pin 50 comes to a halt caught on the shoulder within rocker plate 52 and, at this point, continued movement of housing 10 to the left causes plate 31 to start pressing on the base of pressurised canister 2. As can be seen, stem 33 transmits the force from plate 34 and the entire canister 2 is moved to the right with respect to the housing in which it is placed. The valve stem at the top is accordingly pressed down and material may be released through nozzle 16.

The device shown in FIGS. 6 to 9 operates analogously save that, in this particular case, the mechanism for actuating the dispenser is quite different. In the case of the device shown in FIGS. 2 to 5, movement of housing 10 relative to housing 40 is achieved by e.g. engaging the user's finger over a lateral post 80 formed integrally with cap 13 and side wall 10. This is not always a most convenient action and in FIGS. 6 to 9, a device is shown which can provide a dispensed dose of medicament located in pressurised canister 2 by squeezing two parts of an outer housing together. This is easier to achieve by certain classes of use, for example those whose manual dexterity is impaired by weakness or disease such as arthritis.

Figure 6:
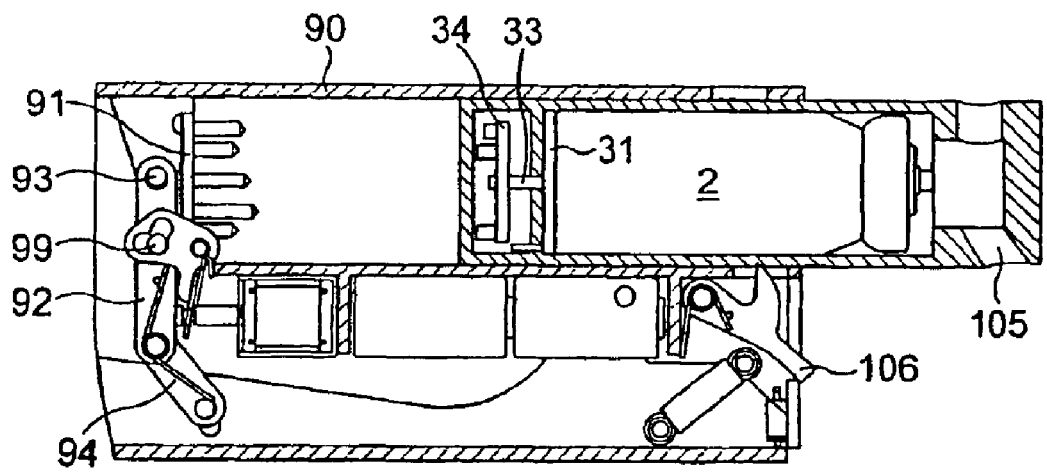

As shown in FIGS. 6 to 9, the outer housing consists of a base portion 90 having a cylindrical cavity in which outer container 10 may be fitted. At one end of the cylindrical cavity, there is provided a key disc 91 which may be moved to the right as shown in FIG. 6 by a lever 92 pivoted at 93 to the back of the disc 91. Lever 92 is itself pivoted to a link 94 having a transverse stud at its end 95 which is slotted into an actuating bar 96 which can pivot around a pivot point denoted 97 in FIG. 8 to the position shown in FIG. 8 and back again. A post 99 on link 92 may move freely within a slot in a rockable plate 100 which is rockable about an axis 101 by means of a solenoid 102.

Figure 7:
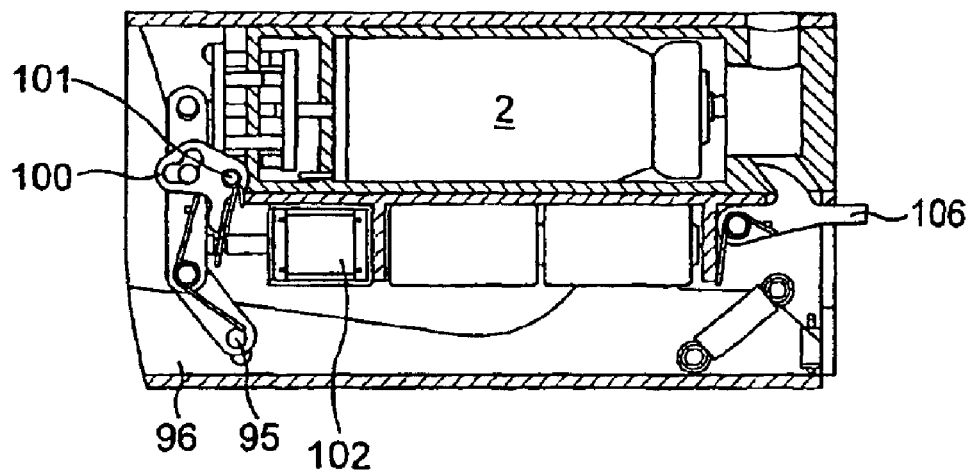
Figure 8:
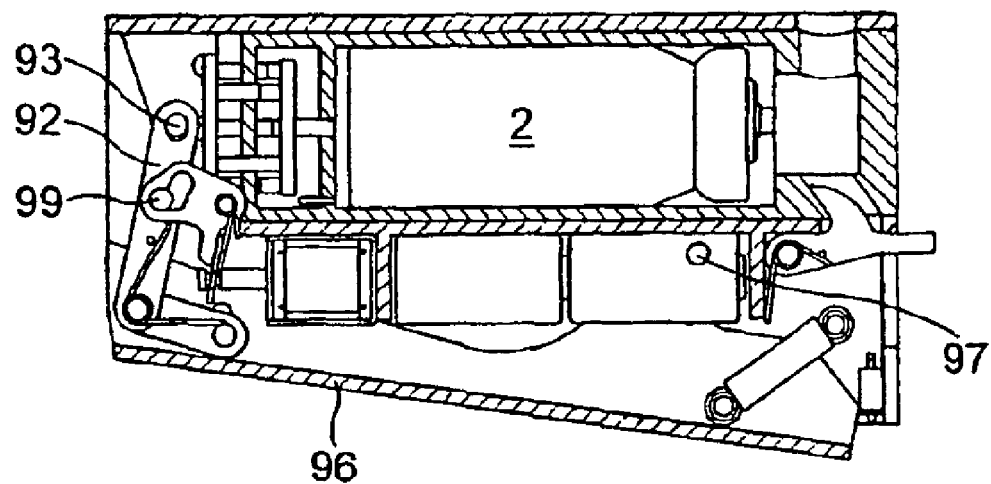
Figure 9:
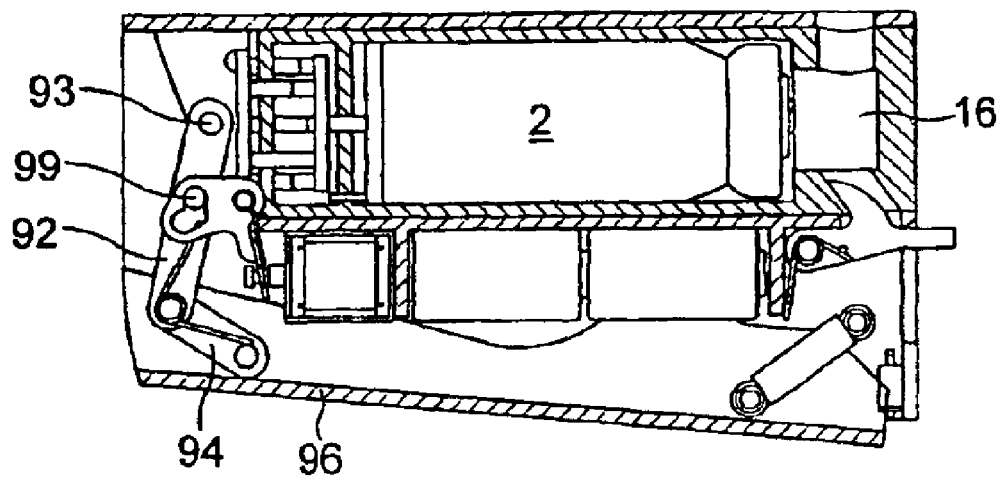

As shown in FIG. 8, if bar 96 is moved up at its left-hand end as seen in the drawing, normally post 99 merely moves to the left and link 92 swivels about pivot 93. If, on the other hand, the solenoid 102 is actuated, then rocker plate 100 moves around pivot point 101 to the position shown in FIG. 9, and it can be seen that with plate 100 moved into this position, post 99 cannot move radially away from pivot point 101. Instead, as actuating bar 96 is moved upwards at its left hand end as shown in FIG. 9, link 94 causes link 92 to pivot around post 99 which is essentially held stationary. Pivot point 93 accordingly moves to the right, thus moving in turn the disc 91 and, because the poles on the key disc are now engaged with corresponding prongs on plate 34, and stem 33 passes through wall 31 and acts to push container 2 to the right within the housing, thus causing dispensing via nozzle 16 of a single dose. Dispensing can be stopped by releasing the actuation bar 96 and the device then returns to the position shown in FIG. 7.

In this embodiment shown in FIGS. 6 to 9, the secure dispensing assembly consisting of canister 2 and its outer housing has an inclined slot 105 in the cap opposite the dispensing aperture and can be held into the overall body of the device by being engaged by a spring-loaded tooth 106 which is pivotable between the position shown in FIG. 6, for loading or unloading a dispensing assembly from the device, and the position shown in FIGS. 7, 8 and 9, where the tooth is engaged in recess 105 and holds the assembly firmly together.

FIGS. 10 and 11 show a more sophisticated design of the key disc and plate and stem member. As shown, the key disc has a base 110 bearing seven different cross-section pins 111. The plate and stem member consists of a plate 114 adapted to press the base of a dispensing canister, a frangible stem 115 and a set of seven radial arms 116, each of which has at its outer end a short axial post 117 with a depression at its free end. The posts 117 are of different lengths, complementary to the lengths of pins 111. FIG. 12 shows the key disc and plate and stem member aligned with the latter located in a schematically indicated cylindrical casing 120 having a transverse inner wall 121 through which the stem passes, and an end wall 122 having a set of seven apertures in it correspondingly located to the posts 117. Across the end wall 122 is an adhered paper security seal 123. As can be seen in the diagrammatic face views of the key and plate and stem member, the pins 111 are arranged to mirror (as shown in FIG. 12) the posts 117. The end of each pin 111 is pointed.

When the device is used, the sequence of movement to effect dispensing is as shown in FIGS. 13*a* to *c*. The key is first pushed towards the wall 122 and as each pin 111 contacts seal 123, it pierces the seal, leaving a distinctive shape if the seal is e.g. of paper. Each pin 111 then comes to engage the end of a post 117 (FIG. 13*b*). Further movement causes the entire plate and stem member to move to the left relative to the casing 120, so moving the canister (not shown) and effecting dispensing. The maximum amount of movement is achieved (FIG. 13*c*) when the base 110 of the key abuts the seal 123.

Although the above description of specific embodiments relates exclusively to axial compression dispensing devices, it is clear that the key/plate/breakable stem(s) configuration can be used to render more secure other dispensing systems where dispensing is caused to occur by rectilinear movement of a push-button or the like.

What is claimed is:

1. A secure dispensing apparatus which comprises a dispensing device surrounded by a housing, the housing having an aperture registered with a dispensing aperture of the dispensing device, and the dispensing device being actuatable to dispense a dose of material contained within it by a rectilinear movement of an actuation member relative to the housing and acting upon a part of the dispensing device, and wherein between the actuation member and the part of the dispensing device there is located a force-transmitting member having at least one elongate breakable stem located substantially parallel to the direction of movement of the actuation member, and the stem(s) being connected to a pressure plate having a surface configuration on its side facing away from the stem providing a set of surfaces not in a plane transverse to the axis of the stem, and wherein the housing has a set of apertures aligned with the set of surfaces on the pressure plate and means for limiting the amount of movement of the force-transmitting member.

2. The apparatus according to claim 1 wherein the dispensing device is an elongate or discoid container or cassette from which a quantity or unit of material can be dispensed by axial or rotary movement.

3. The apparatus according to claim 1 wherein the breakable stem is a single breakable stem, and wherein the number of apertures in the set of apertures in the housing is 5 to 7 and wherein the apertures are substantially equiangularly spaced around an axis of the single breakable stem.

4. The apparatus according to claim 3 wherein the apertures are substantially equidistant from the axis of the stem in a radial direction.

5. The apparatus according to claim 3, wherein the apertures are of at least two different shapes.

6. The apparatus according to claim 1 wherein the set of apertures in the housing is covered with a frangible seal.

7. A secure dispensing apparatus which comprises an axial compression dispensing device surrounded by a housing, the housing having an aperture registered with a dispensing aperture of the axial compression dispensing device, and having a central chamber surrounding the axial compression dispensing device and of axial length slightly longer than that of the axial compression dispensing device, and means at one end of the chamber movable with respect thereto to compress an axial compression dispensing device located within the chamber, whereby to cause dispensing via the dispensing aperture, wherein the means comprises a central breakable axial stem attached to a pressure plate, the pressure plate having a surface configuration on its side facing away from the axial compression dispensing device providing a set of surfaces not in a plane transverse to the axis of the breakable stem, and a set of apertures in the end of the housing aligned with the set of surfaces of the pressure plate and none of the apertures being coaxial with the breakable stem, and wherein means are provided to limit the amount of movement of the pressure plate away from the end of the outer housing containing the set of apertures.

8. The apparatus according to claim 7 wherein the central breakable axial stem is a single breakable stem, and wherein the number of apertures in the set of apertures in the housing is 5 to 7 and wherein the apertures are substantially equiangularly spaced around an axis of the single breakable stem.

9. The apparatus according to claim 8 wherein the apertures are substantially equidistant from the axis of the stem in a radial direction.

10. The apparatus according to claim 8 wherein the apertures are of at least two different shapes.

11. The apparatus according to claim 7 wherein the set of apertures in the housing is covered with a frangible seal.

12. A secure dispensing apparatus comprising:
   (a) a housing constructed and arranged to surround a dispensing device, the housing including a housing aperture registerable with a dispensing aperture of the dispensing device, and having at least one key aperture constructed and arranged to accept an authorized key;
   (b) an actuation member, moveable relative to the housing in a rectilinear direction and constructed and arranged to cooperate with a part of the dispensing device to permit the dispensing device to dispense a dose of material contained within it;
   (c) a force-transmitting member constructed and arranged to be located proximate to said part of the dispensing device, the force-transmitting member including at least one elongate breakable stem positioned substantially parallel to the direction of movement of the actuation member, the stem being connected to a pressure plate having a surface configuration on a side facing away from the stem and facing the at least one key aperture in the housing, the pressure plate being aligned with the at least one key aperture in the housing allowing an inserted authorized key to contact the surface configuration of the pressure plate, the force-transmitting member moving in response to a pressure from the authorized key to permit dispensing from the dispensing device.

13. The apparatus according to claim 12, wherein the force-transmitting member is constructed and arranged to be located between the actuation member and said part of the dispensing device.

14. The apparatus according to claim 12, wherein the surface configuration provides a set of surfaces.

15. The apparatus according to claim 14, wherein the set of surfaces are not in a plane transverse to the axis of the stem.

16. The apparatus according to claim 12, in combination with the dispensing device, the dispensing device being an elongate or discoid container or cassette from which a quantity or unit of material can be dispensed by axial or rotary movement.

17. The apparatus according to claim 12, wherein the at least one key aperture includes a set of key apertures.

18. The apparatus according to claim 17 wherein the breakable stem is a single breakable stem, and the number of apertures in the set of key apertures in the housing is 5 to 7 and wherein the apertures are substantially equiangularly spaced around the axis of the single breakable stem.

19. The apparatus according to claim 18 wherein the apertures are substantially equidistant from the axis of the stem in a radial direction.

20. The apparatus according to claim 18 wherein the apertures are of at least two different shapes.

21. The apparatus according to claim 12 wherein the at least one key aperture in the housing is covered with a frangible seal.

22. The apparatus according to claim 12, wherein the housing includes a wall constructed and arranged to limit rectilinear movement of the force-transmitting member.

* * * * *